United States Patent [19]

Duhault

[11] 4,237,165

[45] Dec. 2, 1980

[54] TREATMENT OF CARBOHYDRATE METABOLISM DISORDERS

[75] Inventor: Jacques Duhault, Chatou, France

[73] Assignee: Science Union et Cie, Suresnes, France

[21] Appl. No.: 692,653

[22] Filed: Jun. 4, 1976

Related U.S. Application Data

[63] Continuation-in-part of Ser. No. 523,273, Nov. 13, 1974, abandoned.

[51] Int. Cl.³ .......................................... A61K 31/235
[52] U.S. Cl. ........................................................ 424/308
[58] Field of Search ................................ 424/308, 309

[56] References Cited

U.S. PATENT DOCUMENTS 3,607,909  9/1971  Beregi .................... 424/309 R X

FOREIGN PATENT DOCUMENTS 1658M   1/1963  France .
104CAM  1/1966  France .

OTHER PUBLICATIONS

Pawan, Chem. Abs., vol. 74, 1971, Ab. No. 110306q.
Rodbell, Chem. Abs., vol. 67, 1967, Ab. No. 30476b.
Pawan et al., Nutrition Soc., Proc. London, vol. 30, 1971, pp. 8A–9A.
Nervi, Chem. Abs., vol. 67, 1967, Ab. No. 30474h.
Hirsch, Chem. Abs., vol. 67, 1967, Ab. No. 30475j.
Burrows, Chem. Abs., vol. 67, 1967, Ab. No. 52046x.
Azeraa, Chem. Abs., vol. 67, 1967, Ab. No. 52047y.
Kallio, Chem. Abs., vol. 67, 1967, Ab. No. 52044v.
Dannenburg, Amphetamines and Related Cpds, ed. by E. Costa et al., Raven Press, N.Y., 1970, pp. 597–610.
Whichelow, Amphetamines and Related Cpds, supra, pp. 611–618.
Duhault, Amphetamines and Related Cpds, supra, pp. 619–626.
Papletti Advances in Lipid Res., Acd. Press, vol. 12, 1974, pp. 45, 97–98, 311–313, 334–338.
E. Costa, Amphetamines and Related Cpds., pp. 22, 23, 26, 39–45.
Duhault, Chem. Abs., vol. 68, 1968, Ab. No. 72259t.
Pawan, The Lancet (1), Mar. 8, 1969, pp. 498–499.
Pawan, Amphetamines and Related Cpds, pp. 641–651.

*Primary Examiner*—Anna P. Fagelson
*Attorney, Agent, or Firm*—Gordon W. Hueschen

[57] ABSTRACT

Pharmaceutical compositions containing a compound selected from 1-(3-trifluoromethyl phenyl)-2-($\beta$-hydroxyethyl)aminopropane and 1-(3-trifluoromethyl phenyl)-2-($\beta$-benzoyloxy ethyl)-aminopropane and physiologically acceptable acid addition salts thereof, useful in the treatment of metabolism disorders.

10 Claims, No Drawings

TREATMENT OF CARBOHYDRATE METABOLISM DISORDERS

This application is a continuation-in-part of Ser. No. 523,273 filed Nov. 13, 1974, abandoned.

The present invention relates to pharmaceutical compositions and a method for the treatment of certain metabolic disorders in animals and humans.

More particularly the invention relates a method of normalizing the carbohydrate, triglyceride and the cholesterol level of the blood, which method comprises the administration to a subject suffering from such disorders, of a therapeutically effective amount of a compound of the formula:

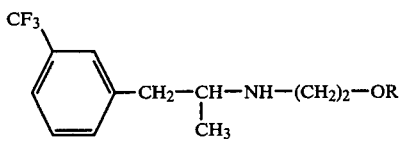

wherein R represents a hydrogen atom or a benzoyl radical

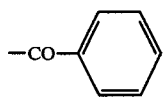

racemic mixtures or optical isomers thereof or physiologically acceptable acid addition salts of the same. Compounds of the above formula are already known from U.S. Pat. No. 3,607,909 and their anorexigenic, analgesic, anticonvulsant properties are described as well as their activity on the plasma FFA level and the epididymal fat.

It was now found that the compounds of the above formula possess a surprising ability to normalize disturbed carbohydrate metabolism in humans and animals as well as to have a pronounced activity on the cholesterol and triglyceride level of the blood.

The results obtained in more than 400 diabetic, prediabetic and obese human patients treated in average by 450 mg daily doses of 1-(m-C $F_3$ phenyl)-2-($\beta$-benzoyloxy ethyl)-aminopropane hydrochloride (780 SE) during 3 to 6 months show that the blood sugar level is decreased and the glucose tolerance test is normalized in the majority of cases. The decrease of triglyceride level was of 30–32%, that of plasma cholesterin of 12% in average.

The results obtained in male rabbits treated with 50 mg/kg/day of 1-(m-trifluoromethylphenyl)-2-($\beta$-benzoyloxy-ethyl)-aminopropane, hydrochloride, for 10 days and then challenged with either 20 microcuries of $C_{14}$ labeled cholesterol having a specific activity of 40 millicuries/millimole, or 100 microcuries of $C_{14}$ labeled sodium acetate having a specific activity of 50 millicuries/millimole, showed that the catabolism of exogenous cholesterol is not modified, the hepatic synthesis of lipids is decreased and that the anabolism of lipids and cholesterol in the aortic wall is decreased. The data are as follows:

|  | Incorporation of 14 C cholesterin | | Incorporation of 14 C acetate | |
|---|---|---|---|---|
|  | control: untreated animals | animals treated with 780 SE | control: untreated animals | animals treated with 780 SE |
| PLASMA total cholesterin | 48 ± 7 | 49,5 ± 5 | 230 ± 6 | 245 ± 15 |
| specific activity | 79 ± 3,5 | 74,3 ± 2,6 | 2818 ± 175 | 2521 ± 722 |
| LIVER total cholesterin | 366 ± 13 | 350 ± 12 | 4960 ± 195 | 4705 ± 55 |
| specific activity | 104 ± 6,5 | 101,5 ± 4 | 2003 ± 72 | 1300 ± 295 p < 0,01 |
| AORTA total cholesterin | 143 ± 3 | 149 ± 3 | 2540 ± 130 | 2285 ± 190 |
| specific activity | 4,26 ± 0,25 | 2,68 ± 0,25 p < 0,001 | 300,5 ± 32 | 184,5 ± 15 p < 0,05 | p = probability of error

The toxicity of the compounds of the invention is very weak. The L $D_{50}$ in mice is 1450 mg/kg P.O. for the benzoyl compound and 183 mg/kg I.P. for the hydroxy compound.

Moreover, chronic toxicity studies after administration during 6 months to rats and dogs did not reveal any alteration in the histologic aspect of the organs of the animals treated with daily doses of 150 mg/kg of the benzoyl compound.

The low toxicity and the above described properties permit the use of the pharmaceutical compositions of the invention in therapy, especially in the treatment of latent diabetes, obesity, arteriosclerosis and generally carbohydrate and certain lipid metabolism disorders.

The compounds of the invention may be administered in the usual pharmaceutical forms of tablets, dragees, capsules, suppositories or injectable solutions, in admixture with appropiate carriers, such, for example, as distilled water, starch, talc, lactose, ethylcellulose, cocoa butter etc.

The doses may vary from 10 to 300 mg, preferably from 20 to 150 mg, 3 to 5 times a day in oral, rectal or parenteral administration.

The following examples illustrate the process for preparing the compounds which are the active principle of the present invention:

EXAMPLE 1

1-(m-trifluoromethylphenyl)-2-($\beta$-hydroxy-ethyl)-amino propane

In an autoclave of 1 l., being held at −20° C., there were added 305 parts of 1-(m-trifluoroethylphenyl)-2-amino propane to 53 parts of ethylene oxide and 37,5 parts of water. After being allowed to warm at room temperature, at which point it was stirred for 1 hour, the reaction mixture was heated to 100°–110° C. and maintained at this temperature for 4 hours.

Distillation of the crude product yielded 154 parts 1-(m-trifluoromethylphenyl)-2-($\beta$-hydroxy-ethyl)-amino propane, B.P. 109°–111° C. at 0.4 millimeters pressure. Acid fumarate m.p. 133° C. (isopropanol).

EXAMPLE 2

1. 1-(m-trifluoromethylphenyl)-2-(β-hydroxy-ethyl)-amino propane 75 parts of dl 1-(m-trifluoromethylphenyl)-2-(β hydroxyethyl)-amino were added to a solution of 147 parts of d (−) dibenzoyl tartaric acid in 1800 parts of ethyl acetate held at reflux while stirring. After being allowed to cool at room temperature, the salt was collected by filtration, washed with ethyl acetate and dried, yielded 95 parts of salt A, which after being twice recrystallized from ethanol, afforded 65 parts of the pure salt, m.p. 154° C.

Liberation of the base from salt A with aqueous sodium hydroxide, followed by extraction with ether, and drying over MgSO₄ gave 23.5 parts of / l-(m-trifluoromethylphenyl)-2-(β-hydroxy-ethyl)amino propane, B.P. 109° C. at 0.7 millimeters pressure. The $[a]_D^{22}$ was −13.7° (C.16, ethanol). Acid fumarate m.p. 135° C. (isopropanol).

EXAMPLE 3 dl-(m-trifluoromethylphenyl)-2-(β-hydroxy-ethyl)-amino propane

The filtrate remaining after separation of salt A of example 2 was concentrated in vacuo and the base liberated. 24 parts were obtained boiling at 111°–115° C. at 1.05–1.1 millimeter pressure The $[a]_D^{22}$ was +6.5 (C. 16; ethanol) 25 parts of this base were treated with 22 parts of d-camphoric acid in 80 parts of ethyl acetate. When crystallization was complete, the solid salt B was collected by filtration and dried, yielding 18 parts of d-acid camphorate, m.p. 126° C.

Recrystallization from 56 parts of ethyl acetate afforded 16 parts of the pure salt, m.p. 127° C.

Liberation of the base from salt B with aqueous sodium hydroxide gave the dextro-rotatory compound, b.p. 111°–112° C. at 0.95 millimeters pressure. The $[a]_D^{22.5}$ was +13,6° (C 16. ethanol). Acid fumarate m.p. 135° C. (isopropanol).

EXAMPLE 4

1-(m-trifluoromethylphenyl)-2-(β-benzoyloxy-ethyl)-amino propane hydrochloride

To a solution of 24.7 parts of 1-(m-trifluoromethylphenyl)-2-(β-hydroxy-ethyl)-amino propane in 140 parts of anhydrous benzene, there were added successively 15 parts of 4.7 N hydrochloric ether and a solution of 14 parts of benzoyl chloride in 24 parts of anhydrous benzene. The addition required 10 minutes, the reaction mixture was then refluxed for 8 hours.

The solid product was collected by filtration and after recrystallization from 230 parts of ethyl acetate, there were obtained 15 parts of 1-(m-trifluoromethylphenyl)-2-(β-benzoyloxy-ethyl)-amino propane hydrochloride melting at 161° C.

10 parts of this hydrochloride are put in suspension in 100 parts of water, 80 parts of ether are added then 10 parts of a concentrated solution of ammonium hydroxide. The mixture is stirred for few minutes until dissolving of the salt, the ethered solution is poured off and dried. After the ether is eliminated under vacuum, 9 parts of 1-(m-trifluoromethylphenyl)-2-(β-benzoyloxy-ethyl)-amino propane are obtained; the base is a colourless oil.

5.5 parts of this base are dissolved in 38 parts of absolute ethanol, and the so obtained solution is added to 2.2 parts of fumeric acid in 90 parts of absolute ethanol. The mixture is heated until dissolving of the precipitate, then cooled. After filtration and drying, 5 parts of fumarate of 1-(m-trifluoromethylphenyl)-2-(β-benzoyloxy-ethyl)-amino propane are obtained, melting at 161°–162° C.

By the same manner, the following compounds were prepared:

(a) d 1-(m-trifluoromethylphenyl)-2-(β-benzoyloxy-ethyl)-amino propane hydrochloride, M.P. 156°–157° C. (isopropanol) starting from d 1-(m-trifluoromethylphenyl)-2-(β-hydroxy-ethyl)-amino propane and benzoyl chloride.

(b) l 1-(m-trifluoromethylphenyl)-2-(β-benzoyloxy-ethyl)-amino propane hydrochloride, M.P. 156°–157° C. (isopropanol) starting from 1-(m-trifluoromethylphenyl)-2-(β-hydroxy-ethyl)-amino propane and benzoyl chloride.

The following examples illustrate the pharmaceutical compositions containing the active principle of the invention:

EXAMPLE 5

| 1-(3-trifluoromethylphenyl)-2-(β-benzoyloxy-ethyl) amino propane | |
|---|---|
| hydrochloride | 0,15 gr. |
| Starch | 0.06 gr. |
| Ethylcellulose | 0,015 gr. |
| Stearate of Magnesium | 0,005 gr. |
| Glucose | 0,40 gr. |
| Talc | 0,06 gr. |
| Ethylalcohol | 0,015 gr. |
| Distilled water | q. s. for 1 tablet or dragee. |

EXAMPLE 6

| 1-(3-trifluoromethylphenyl)-2-(β-benzoyloxy-ethyl) amino propane | |
|---|---|
| methane sulfonate | 0,02 G. |
| Distilled water for injection | q. s. for 5 ml. |

The results in rabbits disclosed on page two hereof show that the action of the products of the invention in a living animal body, which may be in need of a reduction in blood sugar, triglyceride, and plasma cholesterol, upon administration thereto, is by decreasing hepatic lipid synthesis and by decreasing the anabolism of lipids and cholesterol in the wall of the aorta, which in turn means that the products possess an anti-atheromatous action and may accordingly be used in the treatment and prevention of arteriosclerosis which proceeds through the build-up of atheromas in the aortic walls.

I Claim:

1. A method of treating a human patient in need of a reduction in levels of blood sugar, which consists in administering to said human patient an effective amount therefor of a compound selected from the group consisting of
   (A) 1-(3-trifluoromethylphenyl)-2-(β-hydroxy-ethyl) amino propane;
   (B) 1-(3-trifluoromethylphenyl)-2-(β-benzoyloxy-ethyl) amino propane;
   (C) optical isomers thereof, and
   (D) physiologically acceptable acid addition salts thereof.

2. The method as claimed in claim 1, wherein the compound is administered in unit dosage form containing 10 to 300 mg of the active ingredient.

3. The method of claim 2, wherein the compound is administered in unit dosage form containing 20 to 150 mg of the active ingredient.

4. The method of claim 1, wherein the compound is 1-(3-trifluoromethylphenyl)-2-(β-benzoyloxy-ethyl) amino propane, optical isomers, or physiologically acceptable acid addition salts thereof.

5. The method of claim 1, wherein the compound is 1-(3-trifluoromethylphenyl)-2-(β-benzoyloxy-ethyl) amino propane hydrochloride.

6. A method for reducing blood sugar levels and improving tolerance to ingested glucose as indicated by the glucose tolerance test which consists in administering to the patient in need of same an effective amount therefor of a compound selected from the group consisting of 1-(3-trifluoromethylphenyl)-2-(β-benzoyloxy-ethyl)-aminopropane, optical isomers thereof, and physiologically acceptable acid addition salts thereof.

7. The method according to claim 6, wherein human patients are treated with an average dosage amounting to 450 mg daily of 1-(3-trifluoromethylphenyl)-2-(β-benzoyloxy-ethyl)-aminopropane acid addition salt.

8. The method according to claim 7, wherein the acid addition salt is the hydrochloride.

9. The method according to claim 6, wherein the compound is administered in unit dosage form containing 10 to 300 mg of the essential active ingredient.

10. The method according to claim 9, wherein the compound is administered in unit dosage form containing 20 to 150 mg of the active ingredient.

* * * * *